(12) United States Patent
Savinen et al.

(10) Patent No.: US 7,783,002 B2
(45) Date of Patent: Aug. 24, 2010

(54) MEDICAL X-RAY IMAGING APPARATUS

(75) Inventors: Antti Savinen, Espoo (FI); Juhani Martti, Helsinki (FI); Esa Suuronen, Kerava (FI)

(73) Assignee: PaloDEx Group Oy (FI)

( * ) Notice: Subject to any disclaimer, the term of this patent is extended or adjusted under 35 U.S.C. 154(b) by 0 days.

(21) Appl. No.: 12/439,654

(22) PCT Filed: Sep. 5, 2006

(86) PCT No.: PCT/FI2006/050377

§ 371 (c)(1),
(2), (4) Date: Mar. 2, 2009

(87) PCT Pub. No.: WO2008/028988

PCT Pub. Date: Mar. 13, 2008

(65) Prior Publication Data

US 2010/0002832 A1    Jan. 7, 2010

(51) Int. Cl.
*A61B 6/14* (2006.01)
(52) U.S. Cl. ............................ 378/38; 378/39; 378/19
(58) Field of Classification Search ............... 378/4–20, 378/38–40, 193, 197
See application file for complete search history.

(56) References Cited

U.S. PATENT DOCUMENTS

| | | | |
|---|---|---|---|
| 6,118,842 A | 9/2000 | Arai et al. | |
| 6,434,214 B1 | 8/2002 | Kawai et al. | |
| 6,744,847 B2 | 6/2004 | Martti | |
| 2005/0047638 A1 | 3/2005 | Suzuki et al. | |

FOREIGN PATENT DOCUMENTS

| | | |
|---|---|---|
| EP | 1 161 122 A1 | 12/2001 |
| EP | 1 457 155 A1 | 9/2004 |
| JP | 2006034670 A | 2/2006 |
| WO | 99/17659 A1 | 4/1999 |
| WO | 2006/108920 A1 | 10/2006 |
| WO | 2007/018334 A1 | 2/2007 |

OTHER PUBLICATIONS

International Search Report for parent application PCT/FI2006/050377, having a mailing date of May 31, 2007.

*Primary Examiner*—Courtney Thomas
(74) *Attorney, Agent, or Firm*—Andrus, Sceales, Starke & Sawall, LLP

(57) ABSTRACT

The invention relates to a medical X-ray imaging apparatus having a frame part, an X-ray source for producing X-rays, a radiation receiver for detecting radiation transmitted through an object, and a support for supporting the X-ray source and the receiver in positions on opposite sides of the object. The support is connected to the frame part so as to rotate around the axis of rotation provided with actuator means for rotating the support around the said axis of rotation. The apparatus makes possible both panoramic imaging and CT imaging, as selected by the operator. The X-ray apparatus is configured to adjust the ratio of enlargement so as to be optimal for each method of imaging used respectively.

6 Claims, 7 Drawing Sheets

MEDICAL X-RAY IMAGING APPARATUS

CROSS-REFERENCE TO RELATED APPLICATION

This application is the U.S. national stage application of International Application No. PCT/FI2006/050377, filed Sep. 5, 2006, which International application was published on Mar. 13, 2008, as International Publication No. WO 2008/028988 A1 in the English language, which application is incorporated herein by reference.

BACKGROUND OF THE INVENTION

The present invention relates to a medical X-ray imaging apparatus comprising a frame part, an X-ray source for producing X-rays, radiation receiving means for detecting radiation transmitted through an object, support means for supporting the X-ray source and the receiving means in positions on opposite sides of the object, the said support means being connected to the frame part so as to rotate around the axis of rotation, and actuator means for rotating the support means around the said axis of rotation, the apparatus making possible both panoramic imaging and CT imaging, as selected by the operator.

In odontological panoramic X-ray imaging, X-rays emitted from the X-ray source during imaging are guided through the dental arch to the receiving means for producing an image and the support means are rotated to produce an image of essentially the whole dental arch. In panoramic imaging, the aim is to produce images of the teeth in projections that are as perpendicular to the dental arch as possible in order not to produce images of the teeth covering one another. Since the dental arch deviates from a circular shape, the axis of rotation of the support means must be moved during imaging to make perpendicular imaging possible. This type of a panoramic imaging apparatus is known, for example, from the publication U.S. Pat. No. 6,744,847.

In CT imaging, several projection images are taken of the object from different directions, which are then reconstructed to form the desired layer images. A prior art CT imaging apparatus and method are described in the publication U.S. Pat. No. 6,434,214.

A panoramic X-ray imaging apparatus is typically only intended for panoramic imaging and a CT imaging apparatus only for CT imaging and thus an aim in field has been to combine the apparatuses to save on expenses and space. One problem in combining the apparatuses is that the radiation receiving means are located at a standard distance from the focus of the X-ray source, the said distance being a compromise between the different distances required by these two different imaging methods, which means that the ratio of enlargement is not optimal for each imaging method. The ratio of enlargement is determined as the ratio (SID/SOD) of the distance (SID) between the focus of the X-ray source and the image plane (active surface of the detector) to the distance (SOD) between the focus of the X-ray source and the object being imaged (image layer).

SUMMARY OF THE INVENTION

The aim of the present invention is to provide a solution by means of which the above-mentioned problem can be eliminated. To achieve this aim, the X-ray imaging apparatus is characterised by what is stated in the characterising part of claim 1. Further preferable developments of the invention are described in the dependent claims.

BRIEF DESCRIPTION OF THE DRAWINGS

The invention is described in greater detail in the following, with reference to the accompanying drawings, in which.

DETAILED DESCRIPTION OF THE DRAWINGS

Figure 1:
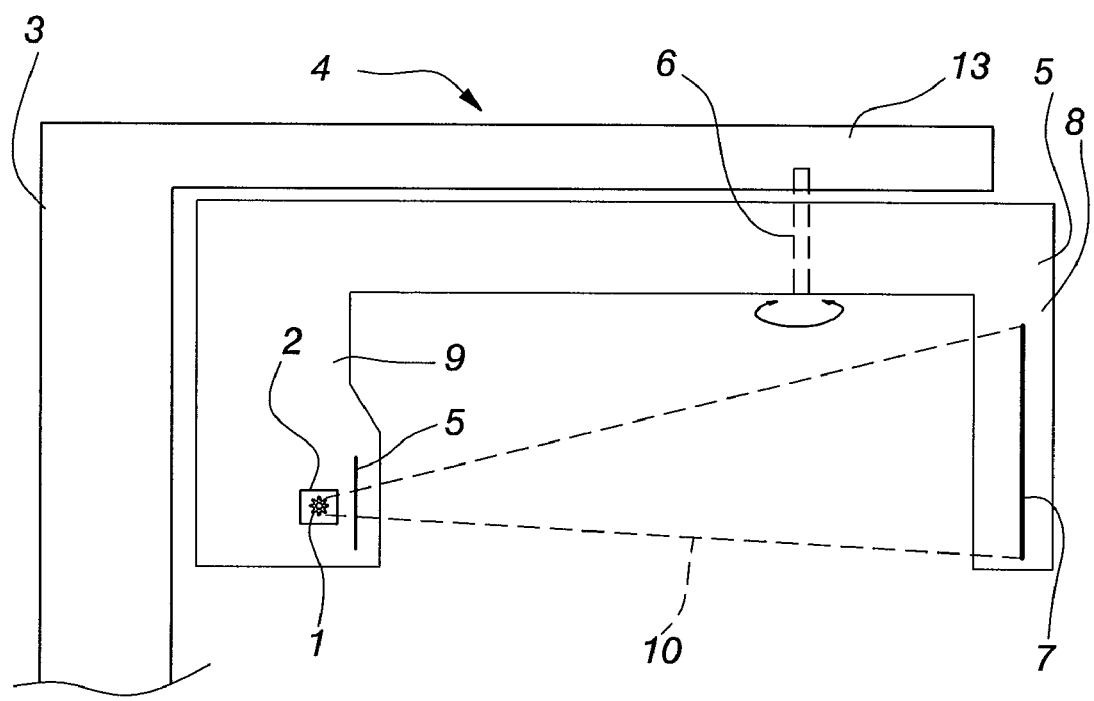
FIG. 1 shows a diagrammatic side view of a panoramic X-ray imaging apparatus according to the prior art.

FIG. 1 shows a panoramic X-ray imaging apparatus of the prior art as a diagrammatic view in principle. The apparatus comprises a vertical frame 3 and a horizontal frame part 4 arranged to reciprocate vertically with respect to it, to which frame part are connected support means 5, 8, 9 turning about the axis of rotation 6. On one branch 9 of the support means is arranged an X-ray source 2, the focus of which is indicated by reference numeral 1. The X-rays 10 emitted from the focus are directed through the object (not shown) being imaged to the X-ray receiving means 7, which may be for example a CCD detector, a CMOS detector, an image plate or an X-ray film, located on the other branch 8 of the support means. The apparatus comprises means (not shown) for turning the support means about the axis of rotation 6 and means for moving the axis of rotation 6 during imaging to allow for as perpendicular imaging as possible with respect to the dental arch. The X-ray apparatus may be realised as a dual-purpose apparatus which also makes possible CT imaging, in which case the receiving means 7 is a flat panel detector by means of which X-ray imaging is performed by irradiating the entire surface area of the flat panel detector or a section of the surface area by means of simultaneous irradiation, which may be repeated from one or more imaging angles, if necessary.

Figure 2:
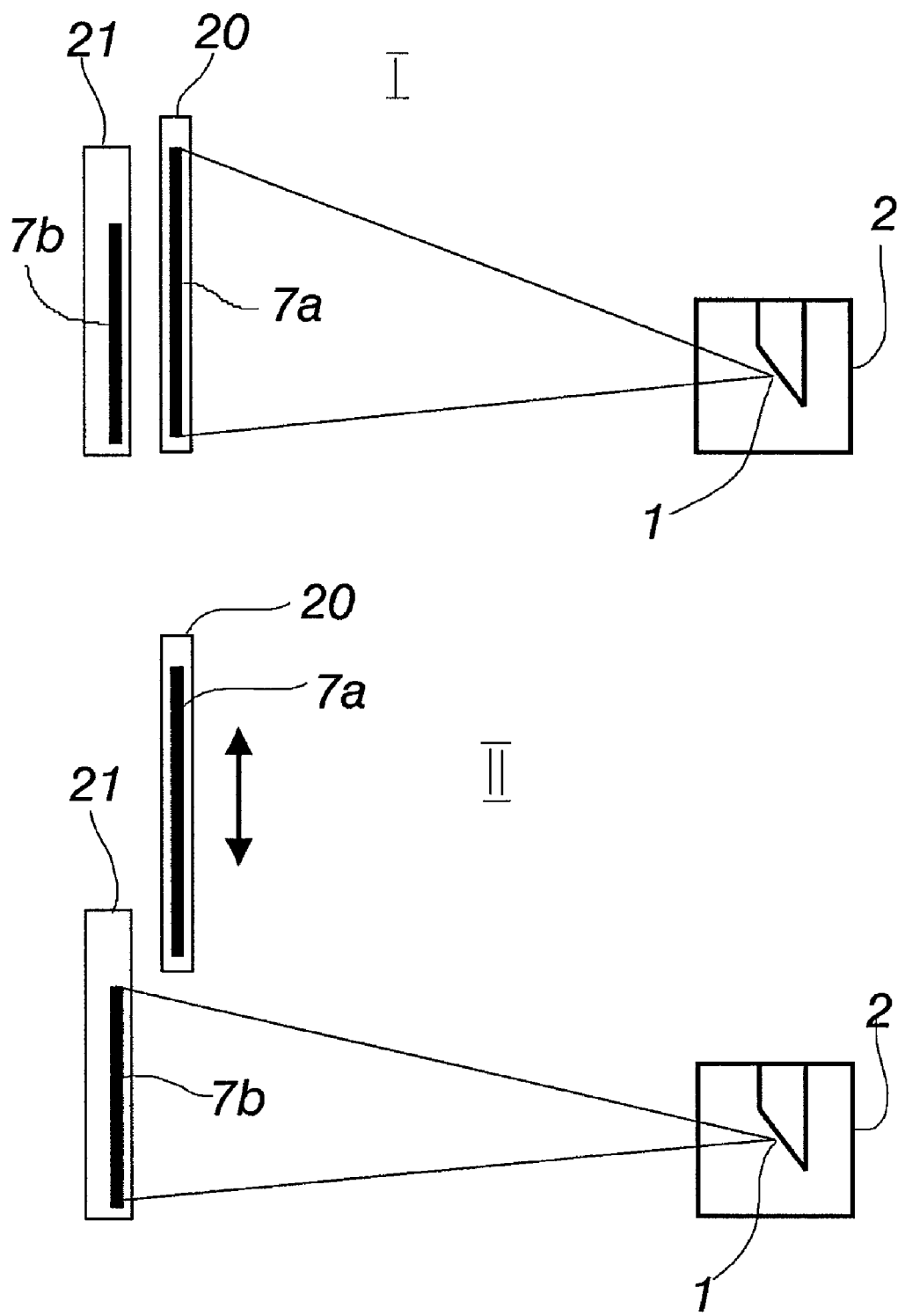
FIGS. 2 to 6 show diagrammatically some embodiments of the invention as views in principle.

FIG. 2 shows a side view in principle of an implementation according to the invention for optimising the ratio of enlargement for each imaging method, where the support means are provided with two cameras 20, 21, one of the cameras 21 being fixed and the other 20 movable. In the embodiment of FIG. 2, the camera 20 is arranged to be movable on an essentially vertical plane to the position indicated by reference numeral I in FIG. 2, where the X-rays emitted from the focus 1 of the X-ray source hit the detector 7a of the movable camera 20 and to position II, which is to the side of the path of the rays, where the rays hit the detector 7b of the fixed camera to perform CT imaging. The fixed camera 21 is preferably inside, for example, the branch part 8 of the support means 5 of the apparatus according to FIG. 1, while the movable camera 20 is located at a point in front of the branch part 8, between the X-ray source 2 focus 1 and the fixed camera 21. The movable camera may be arranged to be movable along the inner surface of the branch part 8 directed towards the branch part 9. By means of this solution can, in a relatively simple manner, be realised the positioning of the detector 7a required for panoramic imaging at an optimal distance from the focus 1 of the X-ray source 2.

Figure 3:
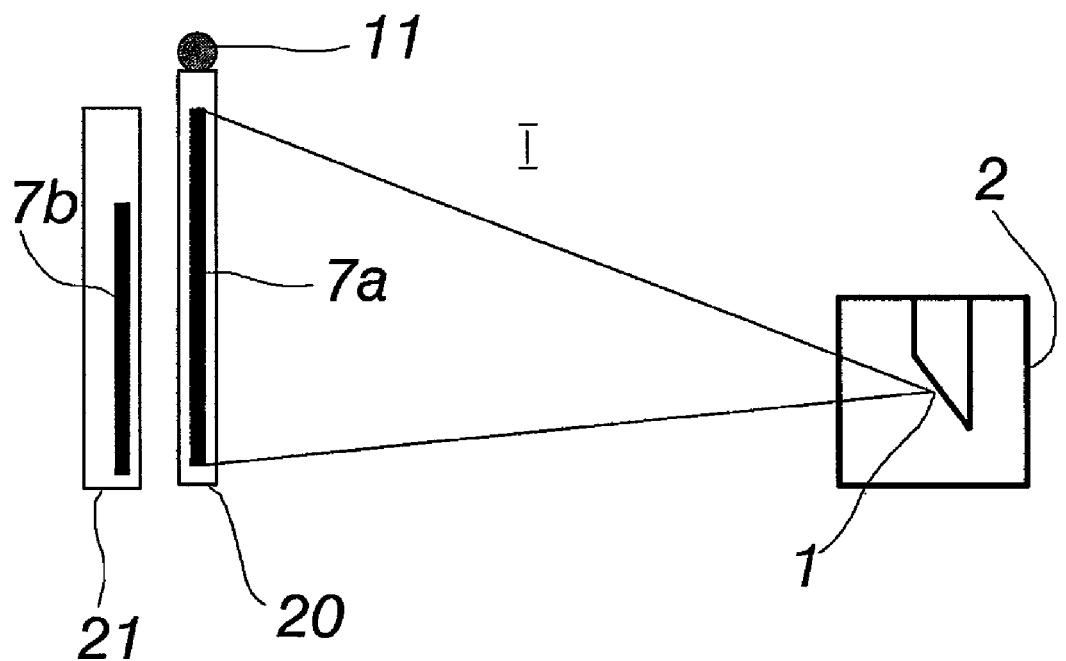
Figure 3:
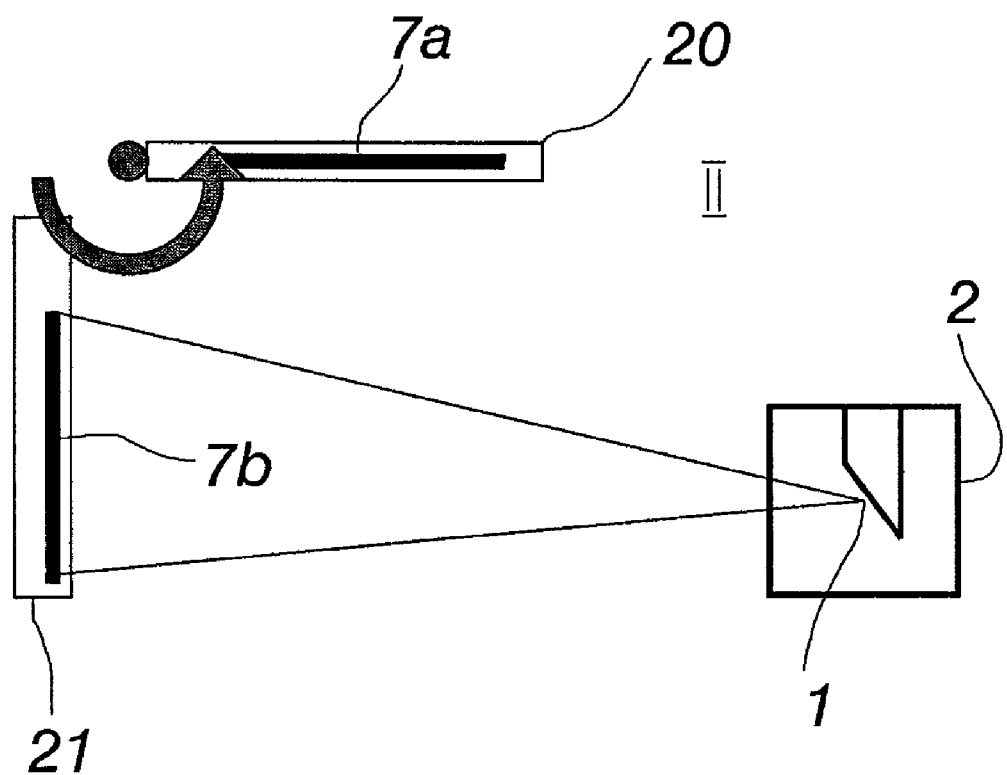

FIG. 3 shows a side view in principle of another embodiment, where the movable camera 20 is arranged to turn about a pivoting axis 11 transverse with respect to the direction of travel of the X-rays from position I making possible panoramic imaging to position II making possible CT imaging, where the movable camera 20 is turned to the side from the path of the X-rays.

Figure 4:
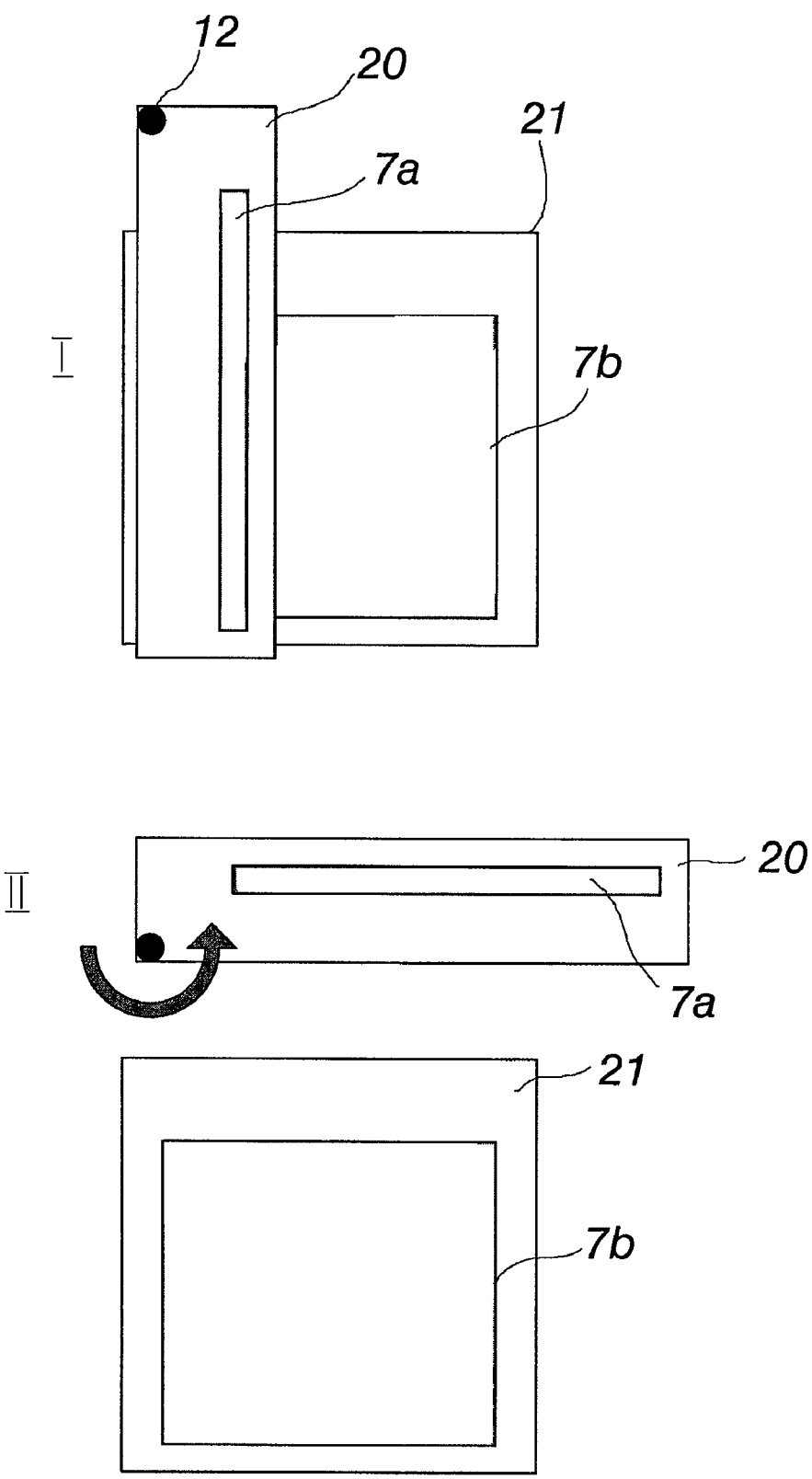

FIG. 4 shows a principle similar to that of FIG. 3, but with the movable camera 20 arranged to turn about a pivoting axis 12 essentially parallel with the X-rays, in a transverse direction with respect to the path of the X-rays. FIG. 4 is depicted as seen from the X-ray source towards the cameras 20, 21.

Figure 5:
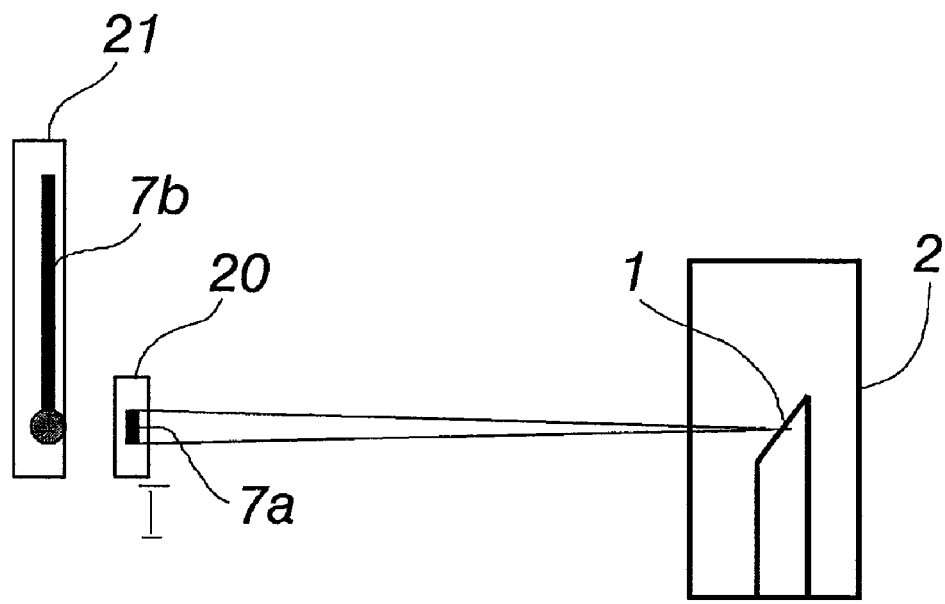
Figure 5:
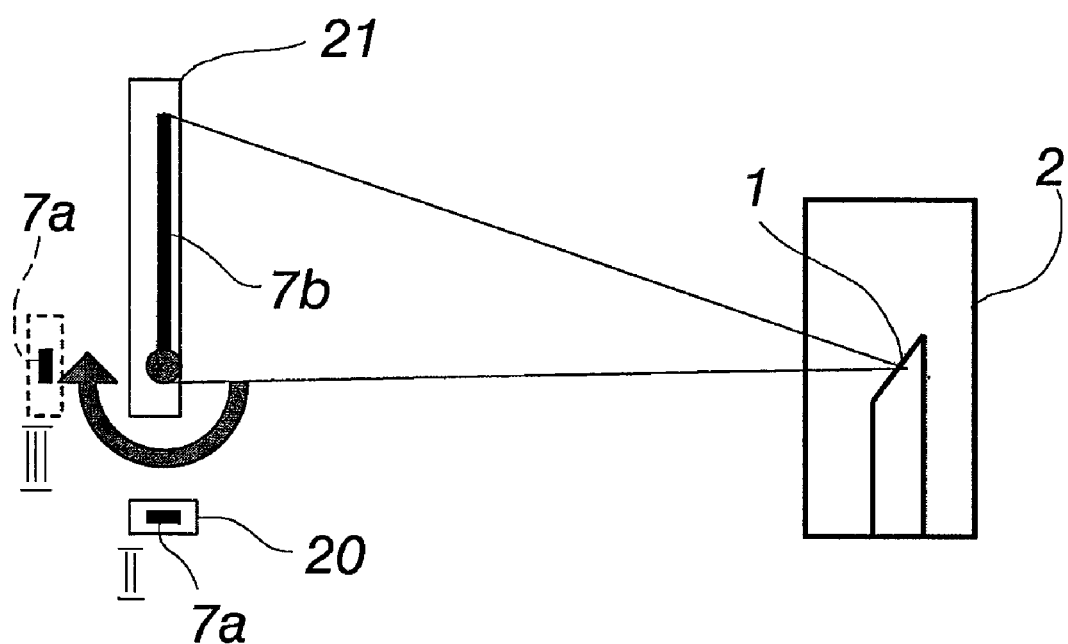

FIG. 5 shows yet another embodiment as a top view in principle, where the movable camera 20 is arranged to turn about the fixed camera 21 from point I on the path of the X-rays to point II (90° when turned) adjacent to the fixed camera 21 or to point III (180° when turned) behind it. The turning movement of the camera 20 may take place, for example, along the path of a circle, about the vertical axis or, for example, a guide groove may be formed in the support means, along which the camera 20 may be moved, along the desired, curved path, around the fixed camera 21.

Figure 6:
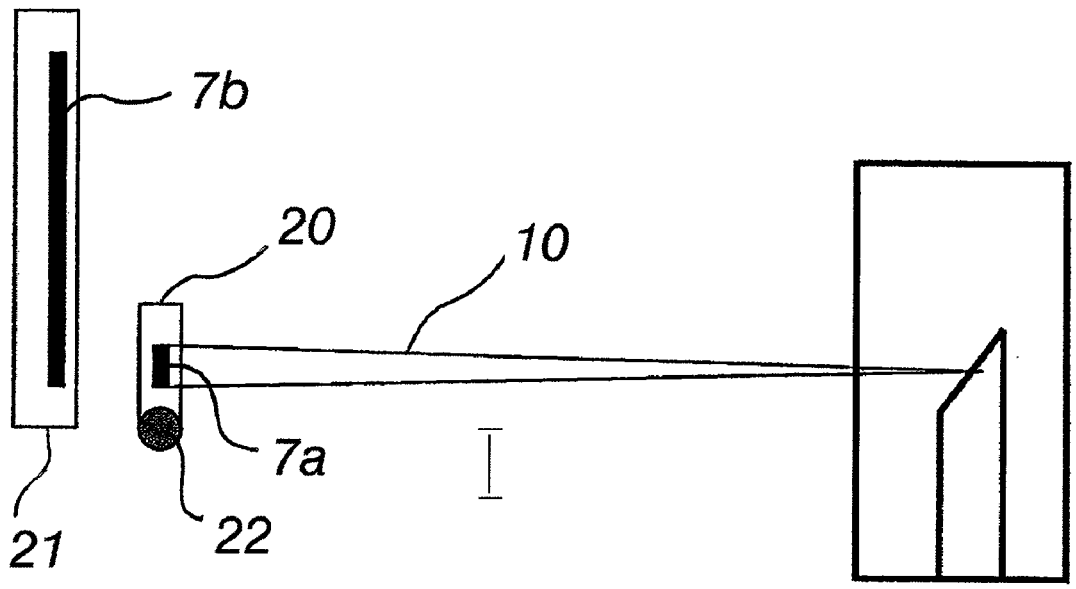
Figure 6:
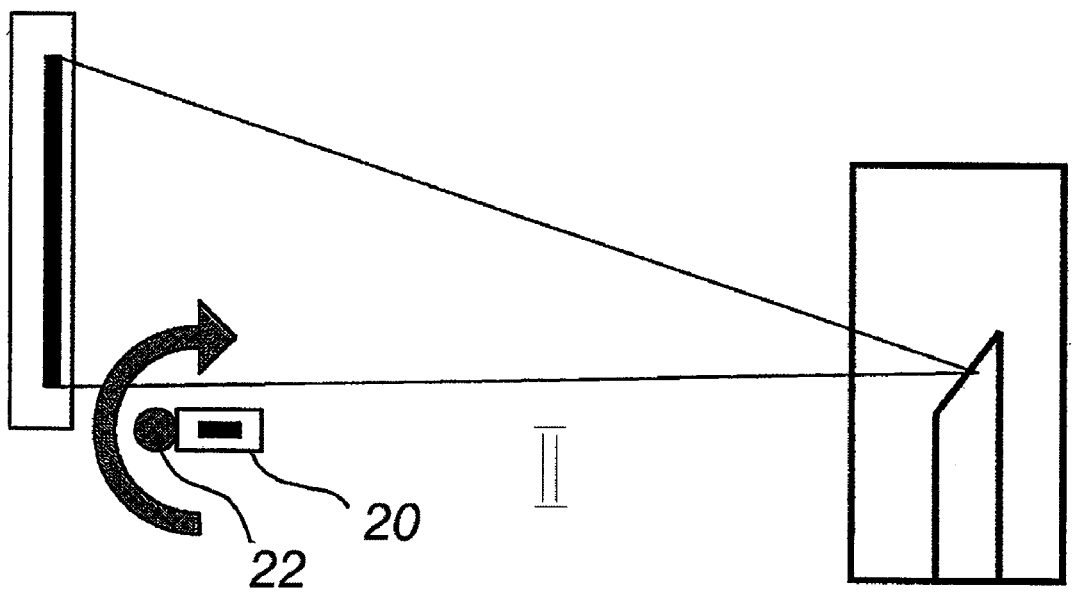

FIG. 6 shows a top view In principle of yet another embodiment, where the movable camera 20 is arranged to turn about an essentially vertical pivoting axis 22 arranged in conjunction with the camera from position I making possible panoramic imaging to position II making possible CT imaging, where the movable camera 20 is turned away from the path of the X-rays.

In the above embodiments, in the panoramic imaging mode, where the movable camera is turned to a point on the path of the X-rays, any radiation possibly passing the movable camera and reaching the detector of the fixed camera is disregarded.

Figure 7:
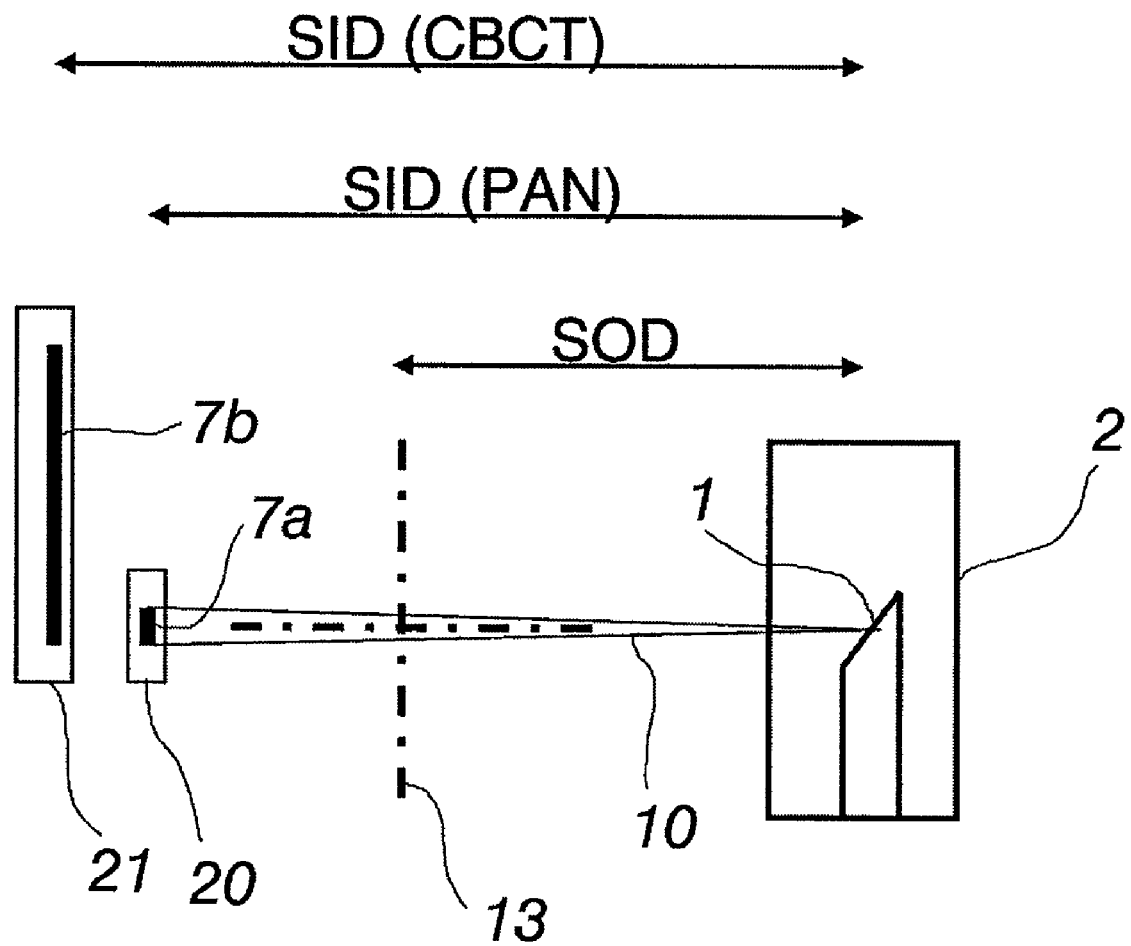
FIG. 7 shows the terms used in determining the ratio of enlargement.

FIG. 7 shows concepts that are central to determining the ratio of enlargement. The ratio of enlargement is determined as the ratio of the distance SID between the focus 1 of the X-ray source 2 and the active surface of the detector 7a or 7b to the distance SOD between the focus 1 and the layer 13 being imaged. In panoramic imaging, SID is shorter than in CT imaging, which means that in panoramic imaging, the ratio of enlargement is smaller than in CT imaging.

The invention claimed is:

1. A medical X-ray imaging apparatus comprising a frame part, an X-ray source for producing X-rays, radiation receiving means for detecting radiation transmitted through an object for forming image information, support means for supporting the X-ray source and the radiation receiving means in positions on opposite sides of the object, said support means being connected to the frame part so as to rotate around the axis of rotation, and actuator means for rotating said support means around the said axis of rotation, the apparatus configured for both panoramic imaging and CT imaging, wherein the apparatus comprises as receiving means for CT imaging a fixed camera which comprises a detector for CT imaging, and as receiving means for panoramic imaging a movable camera, which comprises a detector for panoramic imaging, and the movable camera is arranged to be turned about a pivoting axis, to at least one of a first position between the fixed camera and the focus of the X-ray source on the path of the X-rays, where the X-rays are directed at the detector of the movable camera for performing panoramic imaging, and away from the first position to a second position, where the X-rays are directed at the detector of the fixed camera for performing CT imaging, and where the turning movements are arranged so that a ratio of enlargement is substantially optimal for each method of imaging used.

2. An X-ray imaging apparatus as claimed in claim 1, wherein the X-ray imaging apparatus comprises means for adjusting the ratio of enlargement, by which means the distance (SID) between the active surface of the receiving means and the focus of the X-ray source can be changed to a value optimal for each imaging method, respectively.

3. An X-ray imaging apparatus as claimed in claim 1, wherein the movable camera is arranged to be movable by a vertical linear movement at least to a position on the path of the X-rays, where the X-rays are directed at the detector of the movable camera for performing panoramic imaging, and to a position to the side of the path of the X-rays, where the X-rays are directed at the detector of the fixed camera for performing CT imaging.

4. An X-ray imaging apparatus as claimed in claim 1, wherein the movable camera is arranged to be turned about a pivoting axis transverse to the direction of travel of the X-rays, on a plane essentially parallel to the path of the X-rays, at least to a position on the path of the X-rays, where the X-rays are directed at the detector of the movable camera for performing panoramic imaging, and to a position to the side of the path of the rays, where the X-rays are directed at the detector of the fixed camera for performing CT imaging.

5. An X-ray imaging apparatus as claimed in claim 1, wherein the movable camera is arranged to be turned about a pivoting axis essentially parallel to the X-rays in a direction transverse to the path of the X-rays, at least to a position on the path of the X-rays, where the X-rays are directed at the detector of the movable camera for performing panoramic imaging, and to a position to the side of the path of the X-rays, where the X-rays are directed at the detector of the fixed camera for performing CT imaging.

6. An X-ray imaging apparatus as claimed in claim 1, wherein the movable camera is arranged to be movable along a path rotating around the fixed camera, at least to a position on the path of the X-rays, where the X-rays are directed at the detector of the movable camera for performing panoramic imaging, and to a position to the side of the path of the rays or a position behind the fixed camera, where the X-rays are directed at the detector of the fixed camera for performing CT imaging.

* * * * *